United States Patent [19]

Rao

[11] Patent Number: 5,015,791

[45] Date of Patent: May 14, 1991

[54] CATALYZED HYDROFLUORINATION OF ALKENES

[75] Inventor: V. N. Mallikarjuna Rao, Wilmington, Del.

[73] Assignee: E. I. Du Pont de Nemours and Company, Wilmington, Del.

[21] Appl. No.: 570,951

[22] Filed: Aug. 22, 1990

Related U.S. Application Data

[63] Continuation of Ser. No. 365,166, Jun. 15, 1989, abandoned, which is a continuation-in-part of Ser. No. 210,554, Jun. 23, 1988, abandoned.

[51] Int. Cl.$^5$ .............................................. C07C 17/00
[52] U.S. Cl. ................................................... 570/168
[58] Field of Search ........................................... 570/168

[56] References Cited

U.S. PATENT DOCUMENTS 4,258,225  3/1981  Feiring ................................. 570/168
4,374,289  2/1983  Van Der Puy ..................... 570/168

FOREIGN PATENT DOCUMENTS 0256146  2/1988  European Pat. Off. .
2103392  8/1977  Japan .

OTHER PUBLICATIONS

Feiring, A. E., J. of Fluorine Chem. 13, pp. 7-18 (1979).

Primary Examiner—Alan Siegel

[57] ABSTRACT

Process for the preparation of fluorinated alkanes by contacting alkenes with HF in the presence of $TaCl_2$ or $TaBr_5$.

13 Claims, No Drawings

CATALYZED HYDROFLUORINATION OF ALKENES

CROSS-REFERENCE TO RELATED APPLICATION

This application is a continuation of application Ser. No. 365,166 filed 15, 1989, now abandoned, which is a continuation-in-part of U.S. application Ser. No. 07/210,554 filed June 23, 1988, abandoned.

FIELD OF THE INVENTION

Process for the preparation of fluorinated alkanes by contacting alkenes, preferably halogenated alkenes, with hydrogen fluoride in the presence of $TaCl_5$ or $TaBr_5$.

BACKGROUND OF THE INVENTION

A. E. Feiring, Journal of Fluorine Chemistry, 13, 7-14 18 (1979) discloses the use of tantalum pentafluoride as a catalyst for the addition of hydrogen fluoride to tetra- and trichloroethene and related compounds. The catalyst is also useful for fluorine chlorine exchange reactions. However, under the conditions of the batch experiments, catalysts such as $BF_3$, $TaCl_5$, $Ta_2O_5$, $CoF_3$, $V_2O_5$, $ZrCl_4$, $NbCl_5$, HgO, and $WCl_6$ showed no catalytic activity at 150° C. for the addition of HF to tetrachloroethene.

The use of tantalum pentafluoride as a catalyst for the addition of hydrogen fluoride to unsaturated compounds has been disclosed and claimed in U.S. Pat. No. 4,258,225.

SUMMARY OF THE INVENTION

This invention is a process for the preparation of fluorinated alkanes by contacting, at a temperature of about 0° C. to about 185° C. under substantially anhydrous conditions, one molar equivalent of an alkene, preferably a halogenated alkene, selected from alkenes of the following formulas $$R^1R^2C=CR^3R^4 \text{ and } R^5R^6C=CR^7R^8$$

wherein $R^1$, $R^2$, $R^3$, $R^4$ and $R^5$, $R^6$, $R^7$, $R^8$ are each selected from the group represented by $C_xZ_{2x+1}$, wherein Z is H, F, Br, or Cl and wherein x=0 to 10, preferably with the proviso that in at least one of $R^1$, $R^2$, $R^3$ and $R^4$ and in at least one of $R^5$, $R^6$, $R^7$ and $R^8$, Z is F, Br or Cl; and at least one of the pairs $R^5$ and $R^6$, $R^7$ and $R^8$, $R^5$ and $R^7$, and $R^6$ and $R^8$ taken together is —(CH$_2$)n—wherein "n" is an integer from 2 to 7, with the proviso that when $R^5$ and $R^7$ and/or $R^6$ and $R^8$ are trans, "n" must be 6 to 7, and when only two of the group $R^5$, $R^6$, $R^7$, $R^8$ are combined to form a cyclic structure the remaining two groups may be $C_xZ_{2x+1}$, wherein Z is H, F, Br, or Cl and x=0 to 10,
with HF in the presence of at least one catalyst selected from tantalum pentachloride and tantalum pentabromide to produce a fluorinated alkane.

DETAILS OF THE INVENTION

The resulting fluorinated alkane produced in accordance with the invention has one hydrogen atom over and above the number of hydrogen atoms originally present in the alkene, and one or more fluorine atoms over and above the number of fluorine atoms originally present in the alkene.

The alkene starting materials of the invention do not substantially react with hydrogen fluoride alone under the conditions of temperature and pressure used in this invention and require the presence of added catalyst, specifically tantalum pentachloride ($TaCl_5$) or tantalum pentabromide ($TaBr_5$).

It is preferred that the $TaCl_5$ or $TaBr_5$ be used in an amount from 0.001 to about 5 moles, preferably from 0.001 to 0.250 mole, per mole of starting alkene for reasons of economy and effectiveness. The catalyst is a commercially available crystalline solid and can be used alone or on a support, such as carbon.

The preferred halogenated alkenes are where at least two, and more preferably at least three, of $R^1$, $R^2$, $R^3$ or $R^4$ are Cl. Where at least one of $R^1$, $R^2$, $R^3$ or $R^4$ is $C_xZ_{2x+1}$, it is preferred that x is 1 to 3 and, more preferably x is 1. The specifically preferred alkenes are $Cl_2C=CCl_2$, $HClC=CCl_2$, $HFC=CF_2$, $ClFC=CF_2$, $H_2C=CCl_2$, $H_2C=CF_2$, and $H_2C=CHCl$.

The reaction can be carried out in the liquid phase or vapor phase and at autogenous pressures or under constant pressure ranging from atmospheric to superatmospheric. Both the liquid phase and vapor phase processes include batch, semicontinuous and continuous modes of operation.

The reaction can be carried out at from about 0° C. to about 185° C. The preferred temperature is about 35° C. to about 175° C.

Anhydrous or substantially anhydrous conditions means that water, which is detrimental to the reaction, should be excluded as much as possible from the reaction zone. The HF which is commercially available as anhydrous grade can be used in the reaction directly. Exclusion of moisture from the reaction vessel by means of appropriate moisture traps or other means is a routine procedure and is well known in the art.

It is preferred that 1 to 30 molar equivalents of HF be utilized, and more preferably from 3 to 30 molar equivalents of HF. At least 5 molar equivalents of HF is preferred, particularly for highly chlorinated alkenes such as $Cl_2C=CCl_2$. In practice from 15 to 30 molar equivalents of HF ensures the best combination of economics and fluorination yield.

The reaction vessel is constructed from materials which are resistant to the action of hydrogen halide such as nickel alloys, including monel, "Hastelloy" and "Inconel".

The liquid phase reactions are conducted by introducing the reagents in any order into the reaction vessel. Generally, the $TaCl_5$ or $TaBr_5$ and starting alkene are placed in the reaction vessel which is then cooled, and the required amount of hydrogen fluoride is condensed in the vessel. The vessel may be cooled in Dry Ice or liquid nitrogen and evacuated prior to the introduction of hydrogen fluoride to facilitate addition of the hydrogen fluoride. The contents of the vessel are raised to the appropriate reaction temperature and agitated by shaking or stirring for a length of time sufficient to cause the reaction to occur.

For liquid phase reactions the amount of $TaCl_5$ or $TaBr_5$ used is from 0.001 to about 5 moles per mole of starting alkene, preferably from 0.001 to 0.250 mole, more preferably from 0.005 to about 1 mole per mole of starting alkene but most preferably from 0.01 to 0.5 mole per mole of staring alkene. In general, when one uses the higher molar concentration of the catalyst, he can use a lower molar proportion of the HF reactant. The preferred catalyst is $TaCl_5$. The amount of HF used in the reaction is from 1 to 30 molar equivalents per mole of organic starting material. The reaction can be carried out at from about 0° C. to about 185° C. The preferred temperature is about 35° C. to about 175° C. Reaction time can be from 0.5 to 18 hours; the preferred times are from 1 to 8 hours.

In the vapor phase reaction, the reactants are introduced into the reactor above their boiling points. The temperature of the reactor must also be sufficient to keep the products of the reaction in the vapor state so that they pass over into a cooled receiver beyond the reactor rather than remain in the catalyst zone for a prolonged period of time.

For vapor phase reactions, it is convenient to support the $TaCl_5$ or $TaBr_5$ on an inert porous material such as carbon or other known supports. The preferred catalyst is $TaCl_5$. The amount of catalyst to inert support is from 10% to 50% by weight with amounts of about 25% being preferred. The amount of HF used in the reaction is from 1 to 30 molar equivalents per mole of organic starting material. The reaction can be carried out at from about 50° C. to about 185° C. The preferred temperature is about 70° C. to about 175° C. The contact time of the reagents with the catalyst may be specified instead of reaction time. The combined operations of feed rate, control of reactor temperature and pressure and rate of removal of product from the reactor influence the residence time of the product in the reactor. It may be desirable to shorten the residence time for a given product within the reactor to control the formation of undesired products. Contact time is the average time that the reactant product mixture is in contact with the catalyst. Broadly, contact times of from 0.1 to 25 seconds are useful with preferred contact times in the range of 1 to 10 seconds.

Under the reaction conditions set forth above, a portion of the $TaCl_5$ or $TaBr_5$ may undergo fluorination, so that a portion of the $TaCl_5$ or $TaBr_5$ may be in the form of $TaCl_{5-x}F_x$ or $TaBr_{5-x}F_x$ where "x" may be from 0 to about 5. The instant invention is understood to include that condition when it may exist.

Pressure is not critical. Atmospheric, superatmospheric and autogeneous pressures are the most convenient and are therefore preferred.

The fluorinated alkanes produced by the invention have utility as refrigerants, solvents and blowing agents.

EXAMPLES

General Experimental Procedure

The reactor consisted of a 100 ml high pressure cylinder made of monel or "Inconel" containing a magnetic stirrer and an internal thermocouple. Mounted on top of the reactor was a condenser and a back pressure regulator connected to an optional on line analytical system. Suitable inlet and exit lines were also present to allow for admission of reactants and withdrawal of products.

To the reactor was charged $TaCl_5$ in the desired amount. The reactor was then cooled and evacuated. The alkene starting material and the required amount of HF were then admitted to the reactor. The reactor was then pressurized with nitrogen to the desired pressure while still cold and then gradually brought to the desired operating temperature with stirring by using external heat provided with an oil bath. The back pressure regulator was set to the desired operating pressure prior to heating the reactor.

At the completion of the reaction, the product was isolated by conventional means and analyzed by gas chromatography. All the percentages reported in the Examples are area %.

EXAMPLE 1

The General Experimental Procedure was followed using 16.5 g of tetrachloroethylene, 0.45 g of tantalum pentachloride and 15 9 of anhydrous HF. The reactor was brought to atmospheric pressure with nitrogen. The back pressure regulator was set at 200 psig. The contents were heated and stirred at 119°–122° C. for about four hours. Analysis indicated 43.4% of $CClF_2CHCl_2$, 12.1% $CCl_2FCHCl_2$, and 30.1% unreacted starting material as the major products

EXAMPLE 2

The General Experimental Procedure was followed using 8.3 g of tetrachloroethylene, 2.0 g of tantalum pentachloride and 15 g of anhydrous HF. The reactor was pressurized to 200 psig when cold with nitrogen and the back pressure regulator was set for 400 psig. The contents were heated and stirred at 135°–138° C. for two hours. Product analysis indicated 23% $CF_3CHCl_2$ and 68.9% $CClF_2CHCl_2$ as the major products.

EXAMPLE 3

The General Experimental Procedure was followed using 16.5 g of tetrachloroethylene, 4.0 g of tantalum pentachloride and 15 g of anhydrous HF. The reactor was pressurized to 200 psig with nitrogen and the back pressure regulator was set for 500 psig. The contents were heated and stirred at 142°–144° C. for about one hour. Analysis indicated 69.5% $CF_3CHCl_2$, and 27.4% $CClF_2CHCl_2$ as the major products.

EXAMPLE 4

Example 3 was repeated with the exception that the reaction was run for 90 minutes. Analysis indicated 88.2% $CF_3CHCl_2$ and 9.5% $CClF_2CHCl_2$ as the major products.

EXAMPLE 5

The General Experimental Procedure was followed using 22.4 g of trichloroethylene, 1.0 g of tantalum pentachloride and 10 g of anhydrous HF. The reactor was pressurized to 200 psig with nitrogen when cold and the back pressure regulator was also set for 200 psig. The contents were gradually heated to 85°–90° C. with stirring and maintained at this temperature range for about one hour. Product analysis indicated the presence of 5.3% $CF_3CH_2Cl$, 73.0% $CClF_2CH_2Cl$, 14.9% $CCl_2FCH_2Cl$ and 5.3% starting material in addition to minor amounts of other organics.

EXAMPLE 6

Example 5 was repeated except that 15 g of anhydrous HF was used and the internal temperature was maintained at 78°–80° C. for about two hours with the back pressure regulator set at 500 psig. Product analysis indicated 18.5% $CF_3CH_2Cl$, 75.4% $CClF_2CH_2Cl$ and 5.1% $CCl_2FCH_2Cl$ in addition to small amounts of other organics.

EXAMPLE 7

The General Experimental Procedure was followed using 9.0 g of tetrachloroethylene, 3.0 g of tantalum pentachloride and 7.5 g of anhydrous HF. The reactor was pressurized to 200 psig when cold with nitrogen and the back pressure regulator was set for 500 psig.

The contents were heated with stirring at 144°–147° C. for two hours. Product analysis indicated 66% $CF_3CHCl_2$, 32.7% $CClF_2CHCl_2$, and small amounts of other organics.

What is claimed:

1. A process for the preparation of fluorinated alkanes which comprises contacting, at a temperature of about 0° C. to about 185° C., under substantially anhydrous conditions, one molar equivalent of an alkene selected from alkenes of the following formulas

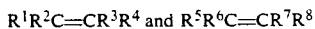

wherein $R^1$, $R^2$, $R^3$, $R^4$ and $R^5$, $R^6$, $R^7$, $R^8$ are each selected from the group represented by $C_xZ_{2x+1}$, wherein Z is H, F, Br or Cl and wherein x=0 to 10; and at least one of the pairs $R^5$ and $R^6$, $R^7$ and $R^8$, $R^5$ and $R^7$, and $R^6$ and $R^8$ taken together is —$(CH_2)_n$— wherein "n" is an integer from 2 to 7 with the proviso that when $R^5$ and $R^7$ and/or $R^6$ and $R^8$ are trans, "n" must be 6 to 7, and when only two of the group $R^5 R^6$, $R^7$, $R^8$ are combined to form a cyclic structure the remaining two groups may be $C_xZ_{2x+1}$, wherein Z is H, F, Br or Cl and x=0 to 10, with HF in the presence of at least one catalyst consisting essentially of tantalum pentachloride or tantalum pentabromide to produce reaction products; removing said reaction products from contact with said catalyst and isolating a fluorinated alkane having one or more fluorine atoms above the number present in said alkene.

2. A process for the preparation of fluorinated alkanes which comprises contacting, at a temperature of about 0° C. to about 185° C., under substantially anhydrous conditions, one molar equivalent of a halogenated alkene selected from alkenes of the following formulas

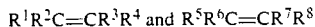

wherein $R^1$, $R^2$, $R^3$, $R^4$ and $R^5$, $R^6$, $R^7$, $R^8$ are each selected from the group represented by $C_xZ_{2x+1}$, wherein Z is H, F, Br, or Cl and wherein X=0 to 10, with the proviso that in at least one of $R^1$, $R^2$, $R^3$, $R^4$, and $R^4$ and in at least one of $R^5$, $R^6$, $R^7$ and $R^8$, Z is F, Br or Cl; and at least one of the pairs $R^5$ and $R^6$, $R^7$ and $R^8$, $R^5$ and $R^7$, and $R^6$ and $R^8$ taken together is —$(CH_2)_n$—. wherein "n" is an integer from 2 to 7 with the proviso that when $R^5$ and $R^7$ and/or $R^6$ and $R^8$ are trans, "n" must be 6 to 7, and when only two of the group $R^5$, $R^6$, $R^7$, $R^8$ are combined to form a cylic structure the remaining two groups may be $C_xZ_{2x+1}$, wherein Z is H, F, Br, or Cl and x=0 to 10, with HF in the presence of at least one catalyst consisting essentially of tantalum pentachloride or tantalum pentabromide to produce reaction products; removing said reaction products from contact with said catalyst and isolating a fluorinated alkane having one or more fluorine atoms above the number present in said alkene.

3. The process of claim 2 wherein the amount of HF is 1 to 30 molar equivalents.

4. The process of claim 2 wherein the catalyst is present in an amount of 0.001 to about 5 molar equivalents.

5. The process of claim 2 wherein the catalyst is tantalum pentachloride.

6. The process of claim 2 wherein the temperature is about 35° C. to 175° C.

7. The process of claim 2 wherein at least two of $R^1$, $R^2$, $R^3$ or $R^4$ are Cl.

8. The process of claim 2 wherein at least three of $R^1$, $R^2$, $R^3$ or $R^4$ are Cl.

9. The process of claim 2 wherein x=1–3.

10. The process of claim 2 wherein x=1.

11. The process of claim 2 wherein the amount of HF is 3–30 molar equivalents.

12. The process of claim 2 wherein the amount of HF is 5–30 molar equivalents.

13. The process of claim 2 wherein the alkene is selected from $Cl_2C=CCl_2$, $HClC=CCl_2$, $HFC=CF_2$, $ClFC=CF_2$, $H_2C=CCl_2$, $H_2C=CF_2$, and $H_2C=CHCl$.

* * * * *